US009939307B2

(12) United States Patent
Hall et al.

(10) Patent No.: US 9,939,307 B2
(45) Date of Patent: Apr. 10, 2018

(54) OPTICAL PROXIMITY SENSOR BASED TOILET WITH FILL TUBE PROXIMITY LEVEL SENSING

(71) Applicants: David R. Hall, Provo, UT (US); Dan Allen, Springville, UT (US); Jared Reynolds, Pleasant Grove, UT (US); Joshua Larsen, Spanish Fork, UT (US); Travis Niederhauser, Mapleton, UT (US); Terrece Pearman, Draper, UT (US)

(72) Inventors: David R. Hall, Provo, UT (US); Dan Allen, Springville, UT (US); Jared Reynolds, Pleasant Grove, UT (US); Joshua Larsen, Spanish Fork, UT (US); Travis Niederhauser, Mapleton, UT (US); Terrece Pearman, Draper, UT (US)

( * ) Notice: Subject to any disclaimer, the term of this patent is extended or adjusted under 35 U.S.C. 154(b) by 0 days.

(21) Appl. No.: 15/337,154

(22) Filed: Oct. 28, 2016

(65) Prior Publication Data
US 2017/0198464 A1    Jul. 13, 2017

Related U.S. Application Data

(60) Provisional application No. 62/280,140, filed on Jan. 19, 2016, provisional application No. 62/276,826, filed on Jan. 9, 2016.

(51) Int. Cl.
*E03D 1/00* (2006.01)
*G01F 23/22* (2006.01)
(Continued)

(52) U.S. Cl.
CPC .............. *G01F 23/22* (2013.01); *A61B 5/021* (2013.01); *A61B 5/208* (2013.01); *A61B 5/4381* (2013.01);
(Continued)

(58) Field of Classification Search
CPC . E03D 5/105; E03D 1/34; E03D 11/13; G01F 23/22; G01F 23/292;
(Continued)

(56) References Cited

U.S. PATENT DOCUMENTS

| 477,716 A | * | 6/1892 | Turner | ..................... E03D 1/34 251/48 |
| 1,555,302 A | * | 9/1925 | McLanahan | ............ E03D 1/266 4/300 |

(Continued)

FOREIGN PATENT DOCUMENTS

| JP | 59220617 A | * | 12/1984 | ........... G01F 23/292 |
| JP | 2016161280 A | * | 9/2016 | ........... G01F 23/292 |

*Primary Examiner* — J. Casimer Jacyna
*Assistant Examiner* — Benjamin R Shaw

(57) ABSTRACT

The present invention is directed to a toilet that includes a slanted fill tube with an optical proximity sensor positioned on or within the inner surface of the fill tube. The optical proximity sensor includes an incoherent light source and a photodiode. The optical proximity sensor as disclosed herein detects small changes in volumes added to a toilet bowl. Consequently, small volumes of excrement that are deposited in the toilet bowl by a user may be detected with greater accuracy. In some embodiments, information about the volume of urine or feces deposited into the toilet bowl is recorded and calculated by a processor. Other sensors, including a toilet bowl water level sensor and a gas sensor may collect data in combination with the optical proximity sensor to provide more complete information about the user's health.

1 Claim, 4 Drawing Sheets

(51) Int. Cl.
*G05D 7/06* (2006.01)
*G01N 33/00* (2006.01)
*G01F 23/26* (2006.01)
*A61B 5/021* (2006.01)
*A61B 5/00* (2006.01)
*G01F 23/292* (2006.01)
*A61B 5/20* (2006.01)
*E03D 11/02* (2006.01)
*A61B 10/00* (2006.01)

(52) U.S. Cl.
CPC ............ *A61B 5/6891* (2013.01); *E03D 11/02* (2013.01); *G01F 23/263* (2013.01); *G01F 23/292* (2013.01); *G01N 33/0047* (2013.01); *G05D 7/0635* (2013.01); *A61B 2010/0083* (2013.01)

(58) Field of Classification Search
CPC ............ G01F 23/2921; G01F 23/2928; G01N 33/0047; G05D 7/0635
USPC .................................... 4/300, 313, 314, 668
See application file for complete search history.

(56) References Cited

U.S. PATENT DOCUMENTS

| | | | | | |
|---|---|---|---|---|---|
| 2,080,073 | A * | 5/1937 | Finley | ............... | E03D 5/026 137/143 |
| 2,625,658 | A * | 1/1953 | Robinson | ............ | G01F 23/2928 250/226 |
| 3,511,572 | A * | 5/1970 | Fortier | ............... | G01F 23/0007 356/496 |
| 3,544,710 | A * | 12/1970 | Poos | ............... | C21B 7/24 348/83 |
| 3,906,554 | A * | 9/1975 | Johnson | ............... | E03D 1/145 4/327 |
| 4,065,227 | A * | 12/1977 | Rose | ............... | G05D 9/12 137/392 |
| 4,297,588 | A * | 10/1981 | Hastbacka | ............... | G01F 23/2921 250/577 |
| 4,322,627 | A * | 3/1982 | Pirlet | ............... | C21B 7/24 250/236 |
| 4,989,452 | A * | 2/1991 | Toon | ............... | E21B 47/042 250/577 |
| 5,073,720 | A * | 12/1991 | Brown | ............... | G01F 23/292 250/577 |
| 5,274,245 | A * | 12/1993 | Lee | ............... | G01F 23/2921 250/577 |
| 5,565,851 | A * | 10/1996 | Richards | ............... | G01F 23/241 137/558 |
| 6,058,519 | A * | 5/2000 | Quintana | ............... | E03D 1/00 137/392 |
| 6,178,569 | B1 * | 1/2001 | Quintana | ............... | E03D 1/00 137/392 |
| 6,367,096 | B1 * | 4/2002 | Quintana | ............... | E03D 1/00 4/427 |
| 6,388,750 | B1 * | 5/2002 | Liu | ............... | G01F 23/292 356/246 |
| 6,661,514 | B1 * | 12/2003 | Tevs | ............... | A01C 7/105 250/222.2 |
| 6,810,902 | B2 * | 11/2004 | Bootka | ............... | E03C 1/242 137/2 |
| 8,362,436 | B1 * | 1/2013 | Mentzer | ............... | G01F 23/292 250/357.1 |
| 2004/0036012 | A1 * | 2/2004 | Horiguchi | ............... | G01J 1/44 250/214 R |
| 2004/0119037 | A1 * | 6/2004 | Mentzer | ............... | G01F 23/292 250/573 |
| 2007/0125162 | A1 * | 6/2007 | Ghazi | ............... | G01F 1/007 73/149 |
| 2010/0200756 | A1 * | 8/2010 | Maiden | ............... | C02F 1/325 250/357.1 |
| 2011/0056290 | A1 * | 3/2011 | Bryant | ............... | G01F 23/292 73/293 |
| 2011/0083504 | A1 * | 4/2011 | Unger | ............... | G01C 9/20 73/304 C |
| 2012/0227173 | A1 * | 9/2012 | Kaikov | ............... | E03D 1/24 4/431 |
| 2012/0279987 | A1 * | 11/2012 | Ophardt | ............... | A47K 5/1205 222/23 |
| 2012/0284910 | A1 * | 11/2012 | Shirakawa | ............... | E03D 11/08 4/420 |
| 2012/0314059 | A1 * | 12/2012 | Hoffmann | ............... | G01F 23/292 348/135 |
| 2014/0353507 | A1 * | 12/2014 | Glaser | ............... | G01F 23/288 250/357.1 |
| 2014/0368823 | A1 * | 12/2014 | Wirthlin | ............... | G01N 21/55 356/448 |
| 2015/0033845 | A1 * | 2/2015 | Cacciola | ............... | G01F 23/2921 73/293 |
| 2016/0122989 | A1 * | 5/2016 | Liu | ............... | E03D 5/10 4/422 |
| 2016/0186420 | A1 * | 6/2016 | Darnell | ............... | E03D 9/05 4/352 |

* cited by examiner

OPTICAL PROXIMITY SENSOR BASED TOILET WITH FILL TUBE PROXIMITY LEVEL SENSING

CROSS-REFERENCE TO RELATED APPLICATIONS

This application claims priority to U.S. provisional patent application Ser. No. 62/280,140 filed on Jan. 19, 2016 and U.S. provisional patent application Ser. No. 62/276,826 filed on Jan. 9, 2016, both of which the entire contents is hereby incorporated by reference.

BACKGROUND

Field of the Invention

This invention relates to toilets, and, in particular, toilets capable of detecting the volume of material added to the toilet bowl.

Background of the Invention

In a toilet configured to refill the toilet bowl up to a point that is below a trap way overflow level, a level sensor may record a level change corresponding to a volume of waste deposited in the toilet bowl. Measuring the urination and defecation volumes may be useful for clinical monitoring as well as for at-home health trending and diet monitoring.

Various level sensors have been proposed for measuring human waste in toilets including capacitive level sensors and laser-based level sensors. One option is the use of laser sensors. However, laser sensors are complicated to integrate and the transition beam has only a linear dependence on the liquid level. A laser potentially requires two ports: laser in and reflection out. Furthermore, a laser is quite sensitive to waves.

In summary, a better location for a toilet bowl level sensor is needed. A level sensor that is sensitive to small changes in volume, causes low hysteresis, and is both easily installed and serviced is also needed.

SUMMARY

We disclose a novel device for measuring a volume of excrement added to a toilet. Measurements of excrement, including urine and feces, may be used to monitor a user's health. The device comprises an optical proximity sensor which may be positioned within a slanted fill tube in a toilet. The optical proximity sensor may include an incoherent light source and a photodiode which, when practiced according to the disclosed invention, may detect smaller changes in volumes added to the toilet bowl, including small urination events. The optical proximity sensor may be positioned on the upper-inner surface of the fill tube or on the lower-inner surface of the fill tube. Each position is within the scope of this disclosure and provides different advantages with regard to practicality, functionality, and ability to measure small changes in volume. In some embodiments, the optical proximity sensor is positioned within a recess within the inner wall of the fill tube. This configuration increases the distance between the optical proximity sensor and the opposite wall of the fill tube and reduces the impact the water's meniscus has on the optical proximity sensor's measurements.

Other sensors may be used in combination with the optical proximity sensor in the fill tube. These include a water level sensor in the toilet bowl and a gas sensor to detect volatile organic compounds (VOCs). The combination of sensors may provide a more detailed description of the excrement added to the toilet bowl and thus collects more informative metrics about the user's health.

The disclosure also describes the use of a processor to record and analyze data collected by the sensors disclosed herein.

DETAILED DESCRIPTION

Definitions

Toilet, as used herein, means a device that may be used to collect one or more biological waste products of a user.

User, as used herein, means a human or animal that deposits bodily waste into an embodiment of the toilet disclosed herein.

Fill tube, as used herein, means a tube or pipe that is connected to a water system and which refills a toilet bowl with water after the toilet is flushed. The fill tube may also be called a refill tube.

Trap way, as used herein, means a section of pipe connecting the toilet bowl to a sewer pipe through which waste passes into the sewer system. The section of pipe is typically curved with the section nearest the toilet bowl holding water when the toilet bowl is full. The section nearest the sewer pipe does not hold water. The trap way may also be called a P-trap or S-trap.

Water seal, as used herein, means a vertical section of a trap way which holds water, the water acting as a barrier for sewer gases which would otherwise travel from a sewer pipe connected to the trap way into the toilet bowl.

Disclosed herein is a toilet capable of measuring small changes in volume within the toilet's hydrostatic circuit. Specifically, the disclosed toilet comprises an optical sensor within a slanted fill tube which detects small changes in volume within the toilet bowl. Consequently, the volume of human excrement, including urine, feces, vomit, or other bodily waste that is deposited into the toilet bowl is detected.

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
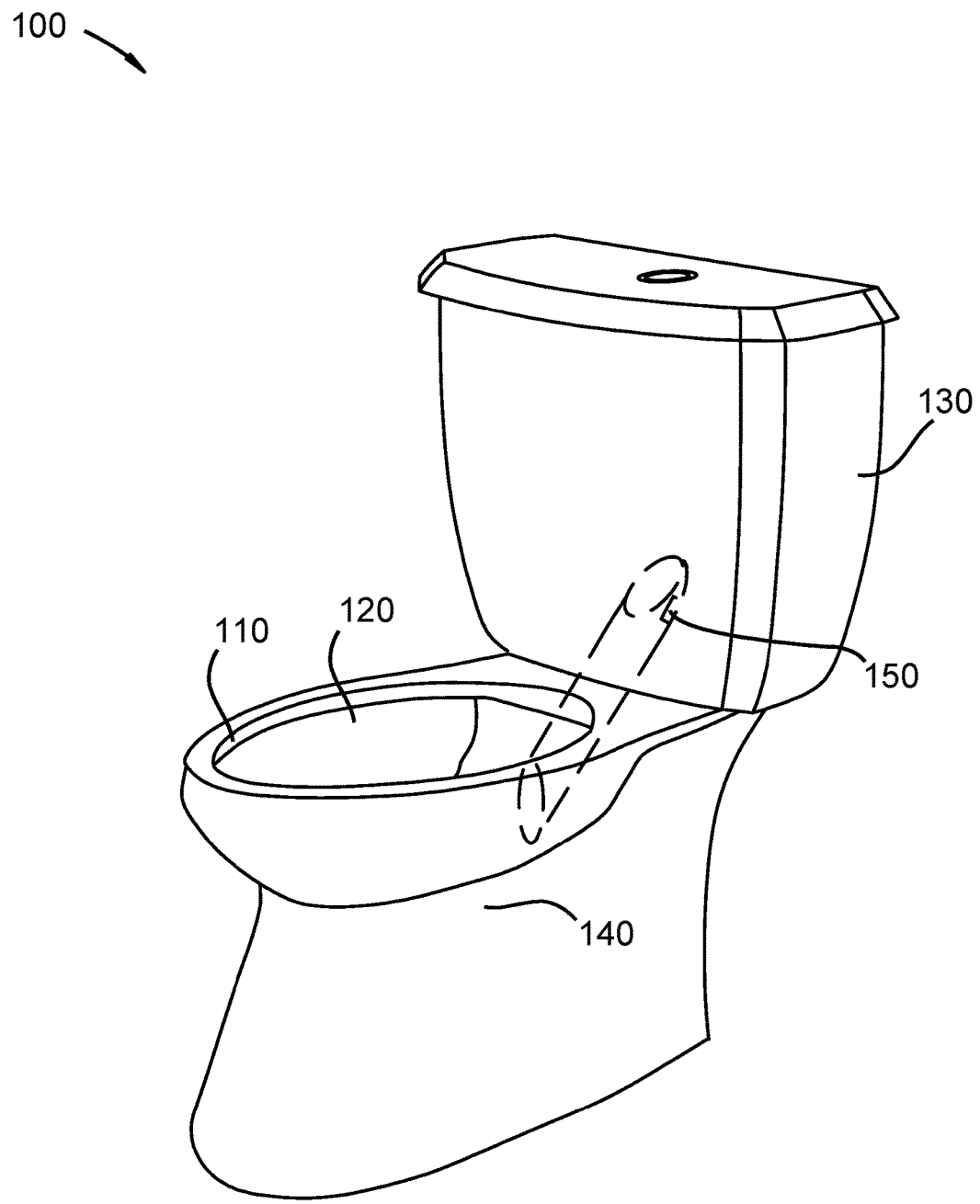
FIG. 1 is a perspective view of a toilet with a slanted fill tube with an optical proximity sensor within the fill tube.

Referring to FIG. 1, toilet 100 is illustrated which includes rim 110, toilet bowl 120, and tank 130. Additionally, toilet 100 includes fill tube 140 which is in a slanted position. Fill tube 140 includes optical proximity sensor 150 on its inner surface. While other embodiments are within the scope of the invention, optical proximity sensor 150 is shown on the lower-inner side of fill tube 140. One of skill in the art will recognize that other parts are included in a toilet, including additional plumbing which is connected to fill tube 140. These have been omitted from FIG. 1 for clarity.

While typical toilets refill up to the level set by the spillway in the trap way ensuring a 2-inch high water seal between the toilet bowl and the sewer pipe, the toilet according to the disclosed invention may include a water seal with a height that his greater than 2 inches. For example, the water seal may be approximately 2.25 inches or approximately 2.5 inches high. In this design, the bowl may refill to a level that is lower than the spillway and still have at least a 2-inch water seal as required for connection to a sewer system. For at least the reason that the toilet bowl has a lower volume of water, it is possible to detect small additions of volume to the bowl, as occur during typical urination and defecation events.

When the optical proximity sensor detects a volume in the toilet bowl that is below the desired water level during refill after flushing, the optical proximity sensor may actuate a refill controller. The refill controller may be a solenoid valve connected to a water supply or other mechanism known in the art. The refill controller may be connected to a water refill valve and cause a water refill valve to stop the flow of water into the toilet bowl when the optical proximity sensor detects a desired level of water in the toilet bowl.

The optical proximity sensor may also detect a clogged toilet. In this embodiment, the proximity level sensor may be in the toilet bowl, the trap way, or the fill tube. However, an advantage of positioning the optical proximity sensor in the fill tube, is that it addresses difficulties associated with detecting a change in liquid level in the spillway, where bodily waste transits. The fill tube is cleaner and experiences less splashing liquid than the toilet bowl. In addition, the fill tube is regularly cleansed by high velocity water from the tank or other high pressure water source, including a jet or wide water pipe. Consequently, the optical window remains clear in this location.

Regardless of the position of the optical proximity sensor within the fill tube, the optical proximity sensor may be removably fixed to the fill tube. Consequently, the optical proximity sensor may be removed and repaired, cleaned, or replaced if damaged or fouled. In some embodiments, a gasket, O-ring, adhesive seal, or other water-repellant sealing means known in the art may be used to seal the optical window mount to the fill tube.

When the water rises above the optical window, the internal reflection of light from the water surface, which is mostly specular, is received by a photodiode and measured. Typically, the signal as measured is analog digital converter (ADC) counts which range from zero to a maximum count value or, in the case of an analog sensor located below the water level, the specular reflection is a small spot and may be approximated as a point source for analysis purposes. Consequently, the intensity light incident on the surface drops off according to the relationship $1/(\text{distance})^2$. This results in a worse case dependence of approximately $1/(\text{distance})^4$. This nonlinear relationship provides a high level of sensitivity to small changes in toilet bowl volume level when the water level is near the proximity sensor. Accordingly, the disclosed invention may be useful for detecting small urination volumes such as those that occur in users that have difficulty urinating due to prostate enlargement.

As the water level rises, sensitivity of the optical proximity sensor gradually drops off until the signal either reaches zero or the liquid level reaches the spillway and stops rising with the addition of more liquid. The output powers of a light-emitting diode (LED) light may also be scaled to increase resolution at longer ranges.

While the optical proximity sensor may comprise of an LED, it may comprise of other incoherent light sources along with a photodiode. Furthermore, the light source and photosensor may have lenses.

Figure 2:
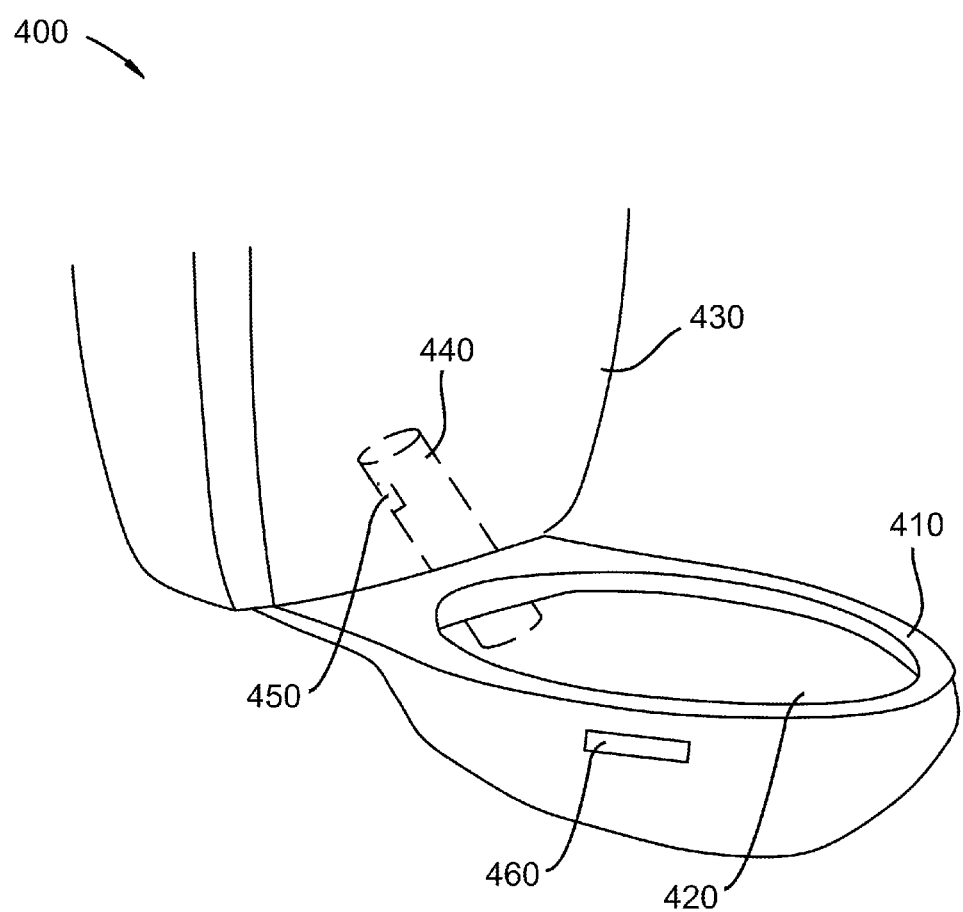
FIG. 2 is an embodiment of a toilet with a slanted fill tube, an optical proximity sensor within the fill tube, and a volume sensor in the toilet bowl

FIG. 2 illustrates toilet 400, which is an embodiment of the invention. Similar to conventional toilets, toilet 400 comprises rim 410, toilet bowl 420, and tank 430. Unlike conventional toilets, toilet 400 further comprise fill tube 440 which includes optical proximity sensor 450. Additionally, toilet 400 includes water level sensor 460 which, in this embodiment, is located within toilet bowl 420. In some embodiments, water level sensor 460 may be a noncontact electrical impedance sensor. By including two sensors in two different positions, a clearer indication of the volume of waste added to the toilet bowl may be obtained.

Figure 3:
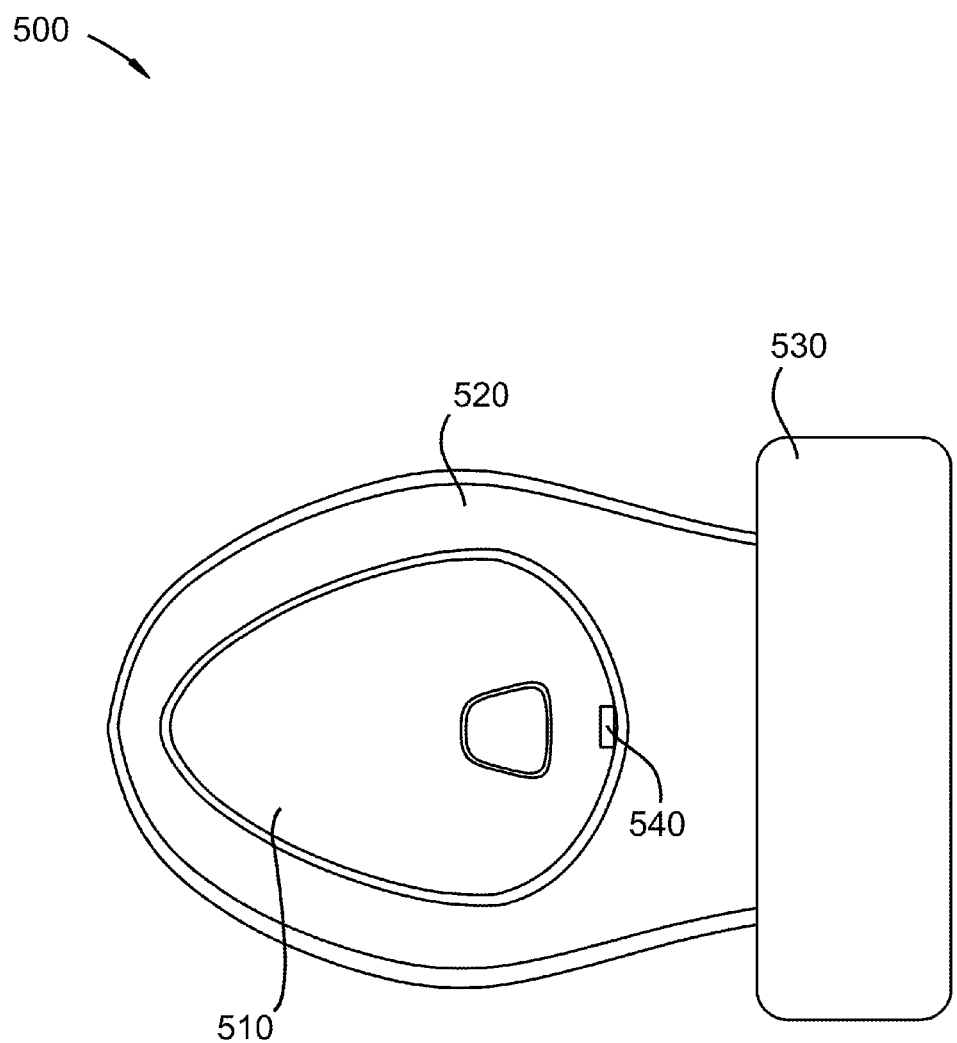
FIG. 3 is a top view of a toilet with a gas sensor according to an embodiment of the invention.

FIG. 3 is a downward-looking illustration of toilet 500, another embodiment of the disclosed invention. Toilet 500 includes toilet bowl 510, rim 520, and tank 530. Toilet 500 further includes gas sensor 540. Gas sensor 540 detects volatile organic compounds (VOCs) which may be produced by flatulence or from fecal matter that has been deposited in the toilet bowl by a user after a bowel movement. Gas sensor 540 and other embodiments thereof may be used in combination with the fill tube and optical proximity sensor as disclosed herein to determine whether a user has had a bowel movement or whether the VOCs detected by a gas sensor are from other sources. For example, when a user has had a bowel movement and deposited fecal matter into the toilet bowl, the gas sensor may detect VOCs and the optical proximity sensor may detect an increase in volume within the toilet bowl. Alternatively, when a user has had an episode of flatulence without an accompanying bowel movement, the gas sensor may detect VOCs but the optical proximity sensor may detect no increase in volume within the toilet bowl. The water level sensor illustrated in toilet 400 of FIG. 2 as well as other embodiments of the disclosed invention may also be combined with a gas sensor and fill tube with optical proximity sensor.

Figure 4:
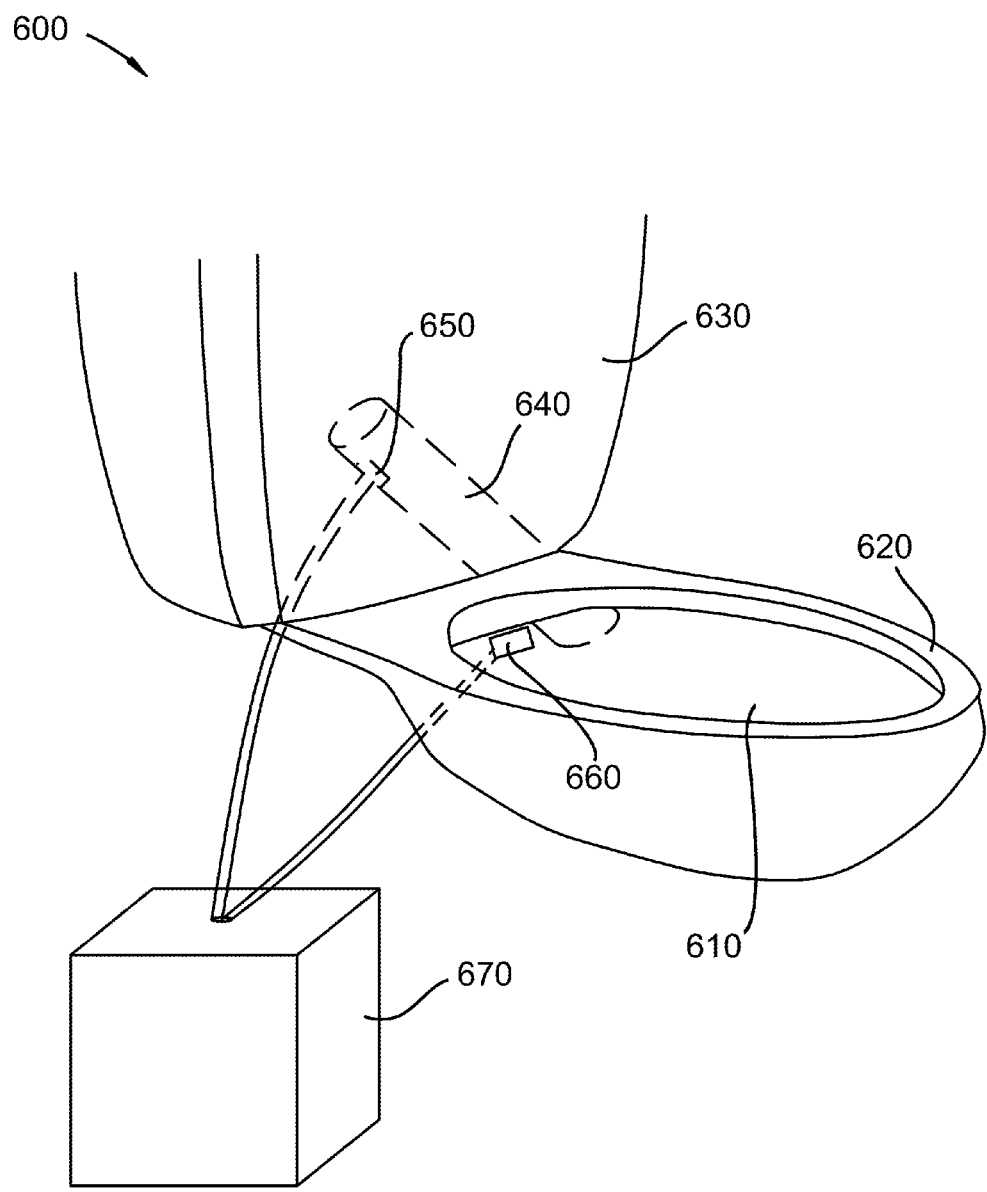
FIG. 4 is a perspective view of a toilet with a slanted fill tube, an optical proximity sensor, a gas sensor, and a processor according to an embodiment of the invention.

FIG. 4 illustrates toilet 600, yet another embodiment of the disclosed invention. Like conventional toilets, toilet 600 includes rim 620, toilet bowl 610, and tank 630. Toilet 600 further includes fill pipe 640, optical proximity sensor 650, and gas sensor 660. Toilet 600 also includes processor 670 which records and processes signals collected by optical proximity sensor 650 and gas sensor 650. Processor 670 may be a microcontroller (MCU) or other electronic controller. Changes in the volume present in toilet bowl 610 and VOCs detected by gas sensor 650 may be recorded and reported by processor 670. Health data may be calculated from signals that enter processor 670 for use by healthcare professionals who may be tasked with monitoring or diagnosing the health status of the user. Lines shown in FIG. 4 which connect both optical proximity sensor 650 and gas sensor 650 to processor 670 indicate signal input which may be through wireless connection, through electrical wiring, or methods for transferring data to a processor that are known in the art.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:
1. A toilet comprising:
   a toilet bowl;
   a fill tube; the fill tube comprising an upper end,
      wherein the fill tube transfers water from a water source into the toilet bowl,
      wherein the fill tube is slanted relative to a vertical line with the upper end of the fill tube directed approximately away from the toilet bowl, and
   wherein the fill tube comprises:
      an optical window, and
      a liquid level sensor, the liquid level sensor comprising an optical proximity sensor, wherein the optical proximity sensor measures a liquid level through the optical window;
   a wastewater exit pipe, wherein the wastewater exit pipe is connected to the toilet bowl and to a sewer pipe via a trap system;
   a gas sensor;
   a water level sensor; and
   a processor, wherein the processor determines either that:
      a user has deposited fecal matter into the toilet bowl when the gas sensor detects volatile organic compounds and the water level sensor detects an increase in volume within the toilet bowl or,
      a user has emitted flatulence without depositing fecal matter into the toilet bowl when the gas sensor detects volatile organic compounds and the water level sensor detects no increase in volume within the toilet bowl.

* * * * *